US005167783A

United States Patent [19]

[11] Patent Number: 5,167,783

[45] Date of Patent: Dec. 1, 1992

Holloway

[54] CAPILLARY GEL ELECTROPHORESIS COLUMNS AND METHOD OF PREPARING THE SAME

[75] Inventor: Robert R. Holloway, Montara, Calif.

[73] Assignee: Hewlett-Packard Company, Palo Alto, Calif.

[21] Appl. No.: 632,278

[22] Filed: Dec. 20, 1990

[51] Int. Cl.$^5$ ....................... G01N 27/26; B01D 57/02

[52] U.S. Cl. .............................. 204/182.8; 204/180.1; 204/299 R

[58] Field of Search .............. 204/182.8, 299 R, 180.1

[56] References Cited

PUBLICATIONS

Stellan Hjertén "High-Performance Electrophoresis: The Electrophoretic Countrpart of High-Performance Liquid Chromatography" Journal of Chromatography 270 (1983)1-6.

*Primary Examiner*—John Niebling
*Assistant Examiner*—John S. Starsiak, Jr.

[57] ABSTRACT

Capillary tubes useful for performing capillary gel electrophoresis separation techniques are prepared by employing prepolymers having one or more terminal functional groups that allow for final polymerization. Use of said prepolymers significantly reduces the amount of shrinkage upon polymerization of said prepolymers to form the electrophoretic gel. The analytical media exhibits strong structural integrity, uniformity, and adheres well to the capillary tubes.

17 Claims, 1 Drawing Sheet

CAPILLARY GEL ELECTROPHORESIS COLUMNS AND METHOD OF PREPARING THE SAME

FIELD OF THE INVENTION

The present invention relates generally to gel electrophoresis and more particularly to gel-containing microcapillary columns for high performance analytical electrophoresis that are substantially free of shrinkage defects.

BACKGROUND OF THE INVENTION

In gel slab electrophoresis, an ionic sample is placed at one end of the column. The ionized components migrate differentially according to charge and bulk under the influence of an axially applied electric field. After a predetermined time, the electric field is removed and the components analyzed according to axial position along the tube.

Capillary zone electrophoresis has proven useful as an efficient method for the separation of certain small solutes. Attractive factors for CZE include the small sample sizes, little or no sample pre-treatment, high solution, automation, and the potential for quantification and recovery of biologically-active samples. Detection and quantitation of the migrating ions can be carried out by measuring, for example, UV absorbance at a particular wavelength. Collection can be made directly into any conducting solution. Microcapillary gel electrophoresis is particularly well-suited for separating proteins and other biopolymers. Very high efficiency and resolving power are possible with capillary gel columns, permitting rapid separation of biopolymers.

The columns of gel can be prepared by filling a tube with an aqueous mixture of acrylamide monomer, and then polymerizing the monomer. In the case of acrylamide, as is generally true in polymer chemistry, the polymer is substantially denser than the original monomer from which the polymer is formed. Accordingly, significant shrinkage occurs during polymerization. For polyacrylamide gel, it is estimated that during polymerization of acrylamide the change in volume is approximately 0.25 ml per gram acrylamide.

As a consequence of this shrinkage, the forming gel has a tendency to pull away from the interior walls of the tube. The voids thus formed between the tube and the gel can disturb the uniformity of an applied electric field, seriously diminish the resolution of the electrophoresis process, and cause local heating. Moreover, the separation of the gel from the tube aggravates a tendency of the gel to migrate out of the tube during electrophoresis. Furthermore, the gel is not homogeneous, in terms of pore size, both radially (center to wall) and longitudinally (end to end).

One common approach with regard to the problem of maintaining the structural integrity of the gel during electrophoresis has been to coat the interior of the tube with a bonding agent which forms covalent bonds between the surface of the tube and the polymer chains. In these microcolumns, a bifunctional silane, for instance, is used as a bonding agent such that one functionality reacts with the inner surface of the capillary and the other (acrylic) functionality reacts with the polymerizing acrylamide monomer network, thus immobilizing the gel matrix. Although separation and resulting migration are mitigated, the tension introduced by the tendency of the gel to shrink during polymerization causes bubble-like voids within the gel itself. This adversely affects the gel's uniformity. These internal voids also distort the applied electric field and diminish the resolution of the electrophoresis process. See Karger et al., U.S. Pat. Nos. 4,865,706.

In a modification of the above approach, microcapillaries are prepared in which the polymeric gel contains hydrophilic polymers. However, the use of the hydrophilic polymer often leads to polymeric gels that are not sufficiently transparent because of phase separation during polymerization. See Karger et al., U.S. Pat. No. 4,865,707, issued Sept. 12, 1989.

The problem of shrinkage has been addressed and partially solved by pressurizing the monomer to its final polymer volume. See Bente, III et al., U.S. Pat. 4,810,456, issued Mar. 7, 1989. Use of pressure polymerization results in a fairly homogenous gel (as viewed under a microscope) but the gel develops "air cores" when it is exposed to a moderate electric field (100 V/cm). It is believed that the inhomogeneities which form during polymerization under pressure are caused by the rapid initiation of polymerization of the reaction due to the more reactive, vis-a-vis acrylamide, acrylic functional group near the wall surface. As the polymerization reaction progresses towards the center of the capillary, acrylamide monomer concentration in the middle of the capillary is decreased, resulting in an inhomogeneous gel.

SUMMARY OF THE INVENTION

It is an object of the present invention to provide capillary tubes with gel based media that are useful for electrophoretic separations of solutes and in which the medium substantially adheres to the surface of the tubes.

It is another object of the invention to provide gel containing capillary tubes in which the gel is homogenous throughout the entire cross section of the capillary.

It is a further object of the invention to provide a method of minimizing the amount of shrinkage or contraction during electrophoretic gel formation by employing prepolymer solutions wherein the prepolymers are moderate to long chain polymers that have one or more terminal functional groups that allow for final bonding or polymerization.

Other objects and advantages of the invention will be apparent to those skilled in the art to which the invention pertains.

These and other objects are accomplished by the inventive method in which inventive prepolymer solutions are used to form electrophoretic gels. The use of the prepolymer solution significantly reduces the amount of shrinkage normally associated with gel formation when monomer solutions are used. In the formation of the electrophoretic gels, the inventive prepolymers can be bonded together by different mechanisms. In one scheme, prepolymer molecules are chemically bonded by polymerization. In another scheme, the prepolymer molecules are chemically bonded (either partially or totally) by molecules that act as linking agents. The inventive electrophoretic gels that are prepared can also be crosslinked.

One preferred prepolymer embodiment is prepolyacrylamide which has the following structure:

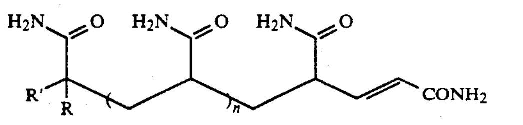

where n is an integer from 1 to 10,000 or more, R is an alkyl or hydrogen, and R' is an alkyl.

As is apparent, the larger the value of n, the degree of polymerization of the prepolyacrylamide or any prepolymer used, the less the shrinkage will be encountered upon gel formation. Using prepolyacrylamide results in a gel that is homogeneous, adheres well to the inner surface of the microcolumn, and exhibits a minimum amount of voids.

One method of synthesizing the inventive prepolymers is via a synthetic pathway commonly referred to as group-transfer polymerization (GTP). GTP involves the repeated addition of monomer to a growing polymer chain end that carries a reactive silyl ketene acetal group.

DETAILED DESCRIPTION OF THE PREFERRED EMBODIMENTS

General Description

Figure 1:
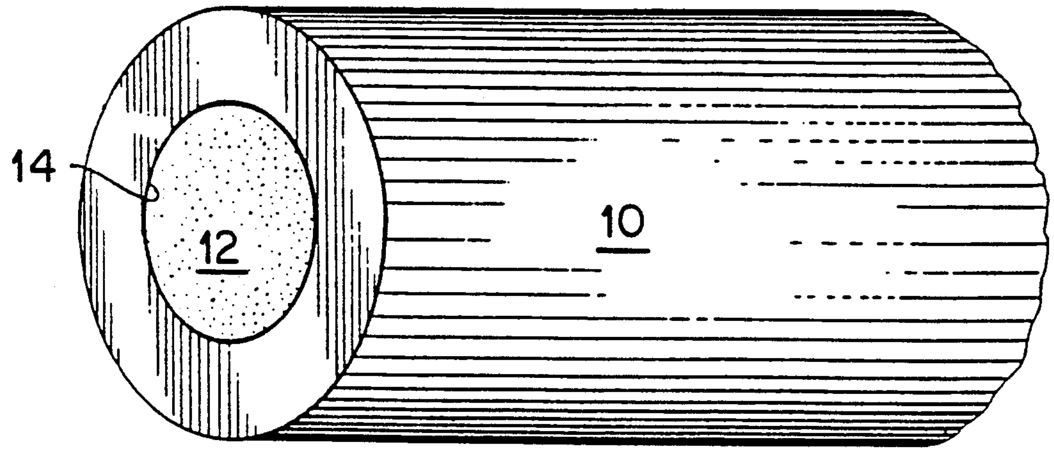
FIG. 1 shows a magnified perspective view of the end of the gel-containing microcapillary of the invention.

The inventive device comprises a gel-containing microcolumn suitable for high performance analytical electrophoresis in which the gel is uniformly distributed within the microcolumn bore and the gel remains stationary within the column under the influence of the high electric field. The homogeneity and structural integrity of the gel are achieved in part by employing prepolymers in the gel-formation process. Hitherto, electrophoretic gels have been prepared by filling a microcolumn bore with a monomer solution and thereafter polymerizing the solution to form the gel. Inevitably, upon polymerization of the monomers, shrinkage or contraction occurs resulting in a gel that does not adhere well to the microcolumn inner surface, and that contains air bubbles or voids. In the formation of conventional polyacrylamide electrophoretic gel, it is estimated that upon polymerization, acrylamide monomers shrink approximately 0.25 ml/gm. However, using prepolymers, each comprising of x acrylamide monomer units, shrinkage would be reduced to approximately 1/x or less (vis-a-vis the monomers). For instance, for a prepolymer of the structure shown in Formula I, it is estimated that upon its polymerization, the shrinkage is only approximately 0.03 ml/gm.

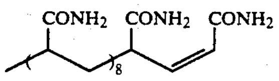

Formula I

As is apparent, the longer the prepolymer chain, that is, the more monomer units are in the prepolymer, the less shrinkage there will be upon polymerization.

The chemical structure of the inventive prepolymers has at least one terminal functional group which allows for final polymerization or bonding. In the formation of electrophoretic gels, the inventive prepolymers can be bonded together by different mechanisms. In one scheme, prepolymer molecules are chemically bonded by polymerization which results in gel comprising polymers having the structure shown in Formula II.

$$PP_1—PP_2—PP_3---PP_{n-1}—PP_n \qquad \text{Formula II}$$

where n is the total number of prepolymer molecules in the gel polymer. The prepolymer units ($PP_x$) need not be identical.

In another scheme, the prepolymer molecules are chemically bonded (either partially or totally) by linking reagent molecules resulting in a gel comprising polymers having the structure as shown in Formula III.

$$PP_1—L_1—PP_2—PP_3—L_2—PP_4---PP_n \qquad \text{Formula III}$$

where n is the total number of prepolymer molecules in the gel polymer. In this polymer, linking molecule $L_1$ bonds prepolymer unit $PP_1$ to $PP_2$ whereas linking molecule $L_2$ bonds $PP_3$ to $PP_4$. Thus with the present invention, the bonding of prepolymers refers to chemical reactions in which prepolymers molecules are covalently attached directly to each other and to chemical reactions in which prepolymer molecules are joined via linking reagents.

In a third scheme, the electrophoretic gel can comprise polymer chains that are crosslinked. In one embodiment, linear polymers analogous to those in Formulas II or III are crosslinked by crosslinking agents. The crosslinking agents may be chemically bonded to the polymer chains either to reactive sites on the prepolymer units or to reactive sites on the linking reagent molecules. It is anticipated that some molecules can function both as crosslinking agents and as linking reagents.

One preferred embodiment of the inventive prepolymer is the prepolyacrylamide which has the structure shown in Formula IV.

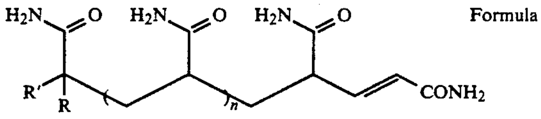

Formula IV

, where n is an integer from 1 to 10,00 or more, R is an alkyl or hydrogen and R' is an alkyl. In this embodiment, the terminal acrylamide allows for free radical polymerization and cross-linking. Other modes of polymerization and free radical may be employed, and $\alpha,\omega$ difunctional (telechelic) prepolymers can also be used, but the final electrophoretic gel would comprise a polyacrylamide. cl Synthesis of Prepolyacrylamide The overall reaction from initial reactants to formation of a prepolyacrylamide is generally illustrated by Reaction Scheme I.

REACTION SCHEME I

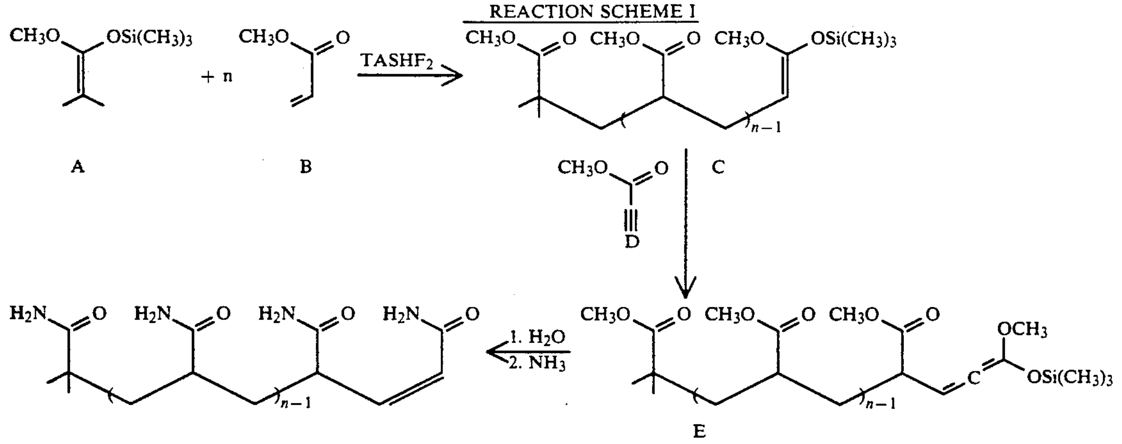

, where n is an integer from 1 to 10,000, or more.

The synthesis of the prepolyacrylamide comprises three principal chemical steps. In the first step, the initiator A reacts with n units of the acrylic monomer B to form polymer C. This reaction is catalyzed by tri(dimethylamino)sulfonium bifluoride ($TASHF_2$). Thereafter, polymer C reacts with alkyne reagent D to form the allene polymer E. Finally, the allene polymer is subject to appropriate quenching reagents, $H_2O$ and $NH_3$ in this case, to yield the prepolyacrylamide. Other suitable catalysts include tri(dimethylamino)sulfonium azide, tri(dimethylamino)sulfonium cyanide, tri(dimethylamino)sulfonium-$(CH_3)_3SiF_2$, tetra t-butyl ammonium flouride, bis-diisobutylammonium oxide, diisobutylammonium chloride, $ZnBr_2$, $ZnI_2$, and $KHF_2$.

An alternative to the above synthesis would be polymerization of another appropriately protected derivative of the amide, for example, the bis trimethylsilylacetamide addition product, which could then be deprotected in a final step.

It is believed that in the above synthesis of polymer C from the initiator and acrylamide monomers, the synthetic pathway can be described by a method commonly referred to group-transfer polymerization (GTP). GTP involves the repeated addition of monomers to a growing polymer chain end that carries a reactive silyl ketene acetal group. During the addition, the silyl group transfers to incoming monomer, regenerating a new ketene acetal function ready for reaction with more monomer. GTP yields "living" polymers at room temperature, "living" polymer being generally a polymer which contains an active terminal group and is capable of further polymerizing in the presence of monomers. See "Group Transfer Polymerization", *Encyclopedia of Polymer Science and Engineering,* Vol. 7, page 580-588 (1987); Farnham et al., U.S. Pat. No. 4,414,372 issued Nov. 8, 1983; and Webster, U.S. Pat. No. 4,417,034 issued Nov. 22, 1983, which are incorporated herein.

Preparation of Microcolumn

As shown in FIG. 1, the inventive device includes a microcapillary 10 and a polymeric gel material 12 within the bore of this microcapillary 10. The gel is substantially free of shrinkage defects and is attached to the inner surface 14 of the microcapillary. The microcapillary 10 of the present invention can be made of any suitable material provided that the detection system to be employed in the electrophoresis can function adequately with the microcapillary material. A preferred material is fused-silica.

Although the invention is not limited by the dimensions of the microcapillary, the dimensions are important in two respects. First, as the internal diameter of the microcapillary is reduced, the electric current and the resultant heating is reduced. Second, the thinner the capillary wall can be made, the better heat transfer from the microcapillary is achieved. Thus, it is desirable that the microcapillary have a minimum internal diameter and also a minimum wall thickness. Capillaries having an internal diameter range from 10 to 200 μm and a wall thickness range less than approximately 200 μm function well. A preferred range of internal diameters is 25 to 100 μm and a preferred range of wall thickness is 25 to 140 μm. A polyimide (or other suitable polymer) coating on the microcapillary permits easy handling of thin-walled capillaries.

The inventive prepolymer employed can be any polymer that has one or more terminal functional groups that allows for final polymerization to form a gel that is suitable for electrophoresis. Normally, the electrophoretic gel will have a pore structure which can be varied by varying the amounts of the inventive prepolymers and the reaction conditions employed. Preferred polymeric gels are cross-linked polymers wherein cross-linking agents are added to the prepolymer solution before polymerization. A preferred cross-linking agent is N,N'-methylenebisacrylamide. Other possible cross-linking agents are N,N'-(1,2-dihydroxyethylene)bisacrylamide, N,N'-diallyltartardiamide, and N,N'-cystamine-bisacrylamide.

The preparation of a preferred embodiment of the gel-containing microcapillary of the present invention comprising a cross-linked polymeric gel is as follows. First, a microcolumn bore is filled with an appropriate prepolymer solution, such as the prepolyacrylamide describe above. Cross-linking reagent N,N'-methylenebisacrylamide is added to the prepolyacrylamide solution. Appropriate catalysts are then added to initiate a polymerization of the prepolyacrylamide in which the N,N'-methylenebisacrylamides are covalently bonded thereto as cross-linkers. The polymerization reaction is preferably initiated with ammonium persulfate and N,N,N',N'-tetramethyleneethylenediamine, although other free radical polymerization initiators (and non-free radical modes such as radiation and electron beam) may be employed as known by those skilled in the art.

As described above, the inventive prepolymers are generally long chain molecules in which repeating monomer moieties form the bulk of the prepolymer. In the case of prepolyacrylamide, the acrylamide monomers can range from 1 to 10,000 or more. Normally, a prepolymer solution to be used to form an electrophoretic gel will comprise prepolymer molecules having different degrees of polymerization. As is apparent, the smaller the values of the degrees of polymerization, the greater the amount of shrinkage during polymerization. However, smaller degrees of polymerization values also allow for greater cross-linkage and lower viscosity. Finally, the prepolymer solution can comprise different prepolymer molecules so that the electrophoretic gel formed comprises block copolymer chains.

The concentrations of prepolymer and cross-linking agent are predetermined according to the porosity of the polymeric gel desired. However, the concentrations of initiator and polymerization catalyst in the reaction mixture are readily determined experimentally. This is done by preparing test solutions containing the desired concentrations of prepolymer and cross-linking agent, but varying the amount of initiator and polymerization catalyst employed These test solutions are allowed to polymerize at the temperature at which the electrophoresis is to be performed and the progress of the polymerization reaction is monitored by ultraviolet spectroscopy by observing the decrease in the absorbance of the vinyl double bond. Alternatively, the microcapillary may be observed visually. Levels of initiator and polymerization catalyst are selected which cause the polymerization to be essentially complete at a reasonable time, approximately within one hour.

It is to be understood that while the invention has been described above in conjunction with preferred specific embodiments, the description and examples are intended to illustrate and not limit the scope of the invention, which is defined by the scope of the appended claims.

What is claimed is:

1. A method of preparing an electrophoretic gel column comprising the steps of:

providing a microcolumn having a bore with an inner surface;

filling the microcolumn bore with a prepolymer solution wherein the prepolymer is a polymer having one or more terminal functional groups that allows for final bonding; and bonding the prepolymers to form a polymeric gel that is substantially free of shrinkage defects and that is substantially bound to the inner surface.

2. The method of preparing an electrophoretic gel column as defined in claim 1 further comprising the step of adding linking reagents to said prepolymer solution to facilitate the bonding of the prepolymers.

3. The method of preparing an electrophoretic gel column as defined in claim 1 wherein the bonding step comprises catalyzing the prepolymer solution to cause polymerization of the prepolymers.

4. The method of preparing an electrophoretic gel column as defined in claim 3 further comprising the step of adding a cross-linking agent to the prepolymer solution prior to catalyzing the prepolymer solution.

5. The method of preparing an electrophoretic gel column as defined in claim 4 wherein the prepolymer is a prepolyacrylamide having the following chemical structure:

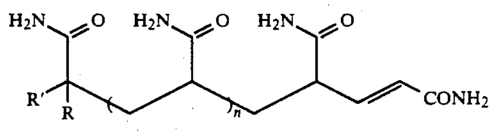

where n is an integer between 1 to about 10,000, or more, R is an alkyl or hydrogen, and R' is an alkyl.

6. The method of preparing an electrophoretic gel column as defined in claim 4 wherein the prepolymer is telechelic.

7. The method of preparing an electrophoretic gel column as defined in claim 5 wherein the cross-linking agent is selected from the group consisting of N,N'-methylenebisacrylamide, N,N'-(1,2dihydroxyethylene)-bisacrylamide, N,N'-diallyltartardiamide, N,N'-cystamine-bisacrylamide, and N-acryloxltris(hydroxymethyl)aminomethane.

8. The method of preparing an electrophoretic gel column as defined in claim 7 wherein the polymeric gel is polyacrylamide.

9. A microcolumn useful for gel capillary electrophoresis comprising:

a tube having a bore with an inner surface; and a polymeric gel disposed in the bore as a substantially continuous phase that is substantially bound to the inner surface wherein the gel remains a substantially continuous phase even under the influence of an high electric field and wherein the gel is formed from a prepolymer solution.

10. The microcolumn as defined in claim 9 wherein the prepolymer is a prepolyacrylamide having the following chemical structure:

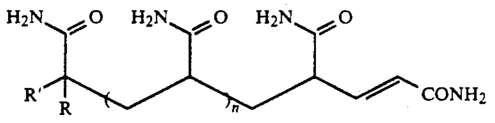

where n is an integer from 1 to about 10,000 or more, R is an alkyl or hydrogen, and R' is an alkyl.

11. The microcolumn as defined in claim 10 wherein the prepolyacrylamide is prepared by:

reacting a mixture of an initiator and monomers to produce a first prepolymer;

reacting the first prepolymer with a reagent to form a second prepolymer; and reacting the second prepolymer with quenching reagents.

12. The microcolumn as defined in claim 11 wherein the initiator has the following chemical structure

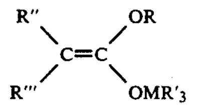

where M is Si, Sn, Ge, or Pb, and R an alkyl or alkyl derivative, R' is hydrogen, an alkyl or alkyl derivative, R'' is hydrogen, an alkyl or alkyl derivative, R''' is hydrogen, an alkyl or alkyl derivative; and wherein the monomers have the following chemical structure:

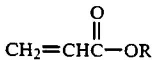

where R is an alkyl or aryl.

13. The microcolumn as defined in claim 11 wherein the initiator is

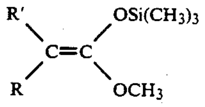

, the monomers are

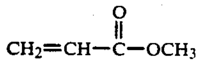

, and the first prepolymer has the following chemical structure

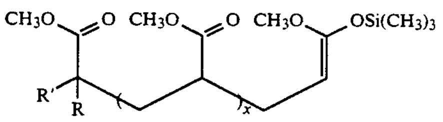

where X is an integer from 1 to about 10,000, or more.

14. The microcolumn as defined in claim 13 wherein the alkyne reagent is

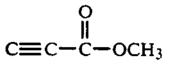

and wherein the second prepolymer has the following chemical structure

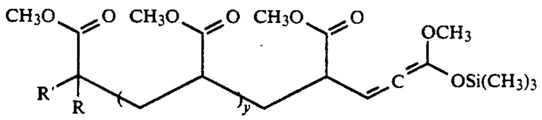

where Y is an integer from 2 to about 10,000, or more.

15. The microcolumn as defined in claim 14 wherein the quenching reagents comprise $H_2O$ and a source of $NH_3$.

16. The microcolumn as defined in claim 15 wherein the catalyst is selected from the group consisting of tri(dimethylamino)sulfonium bifluoride, tri(dimethylamino)sulfonium azide, tri(dimethylamino)sulfonium cyanide, tri(dimethylamino)sulfonium$(CH_3)_3SiF_2$, tetra t-butyl ammonium flouride, bis-diisobutylammonium oxide, diisobutylammonium chloride, $ZnBr_2$, $ZnI_2$, and $KHF_2$.

17. The microcolumn as defined in claim 16 wherein polymeric gel is cross-linked.

* * * * *